(12) United States Patent
Halderman et al.

(10) Patent No.: US 10,514,513 B2
(45) Date of Patent: Dec. 24, 2019

(54) METHOD OF COUPLING OPTICAL FIBER BUNDLES

(71) Applicant: INTUITIVE SURGICAL OPERATIONS, INC., Sunnyvale, CA (US)

(72) Inventors: Jonathan Halderman, Sunnyvale, CA (US); Rumen Deyanov, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/023,858

(22) Filed: Jun. 29, 2018

(65) Prior Publication Data
US 2019/0011648 A1    Jan. 10, 2019

Related U.S. Application Data

(60) Provisional application No. 62/529,040, filed on Jul. 6, 2017.

(51) Int. Cl.
*G02B 6/40* (2006.01)
*A61B 1/00* (2006.01)
*G02B 6/25* (2006.01)

(52) U.S. Cl.
CPC ............ *G02B 6/403* (2013.01); *A61B 1/0011* (2013.01); *A61B 1/00126* (2013.01); *A61B 1/00167* (2013.01); *G02B 6/25* (2013.01)

(58) Field of Classification Search
CPC ......... G02B 6/403; G02B 6/25; A61B 1/0011; A61B 1/00126; A61B 1/00167
See application file for complete search history.

(56) References Cited

U.S. PATENT DOCUMENTS

| | | | | |
|---|---|---|---|---|
| 3,914,015 A | * | 10/1975 | McCartney | G02B 6/403 385/102 |
| 6,330,382 B1 | * | 12/2001 | Harshbarger | G02B 6/14 385/123 |
| 2012/0243830 A1 | * | 9/2012 | Rondeau | G02B 6/3851 385/54 |

OTHER PUBLICATIONS

Vertut, Jean and Philipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Peter Rakowski
(74) *Attorney, Agent, or Firm* — Haynes and Boone, LLP

(57) ABSTRACT

A method and apparatus for coupling fiber bundles. A plurality of fibers are secured within a channel of a fastener system to place the plurality of fibers in a packing configuration within the channel. The fastener system and the plurality of fibers secured by the fastener system are cut through to create a first fiber bundle and a second fiber bundle. The first fiber bundle is coupled with the second fiber bundle.

11 Claims, 11 Drawing Sheets

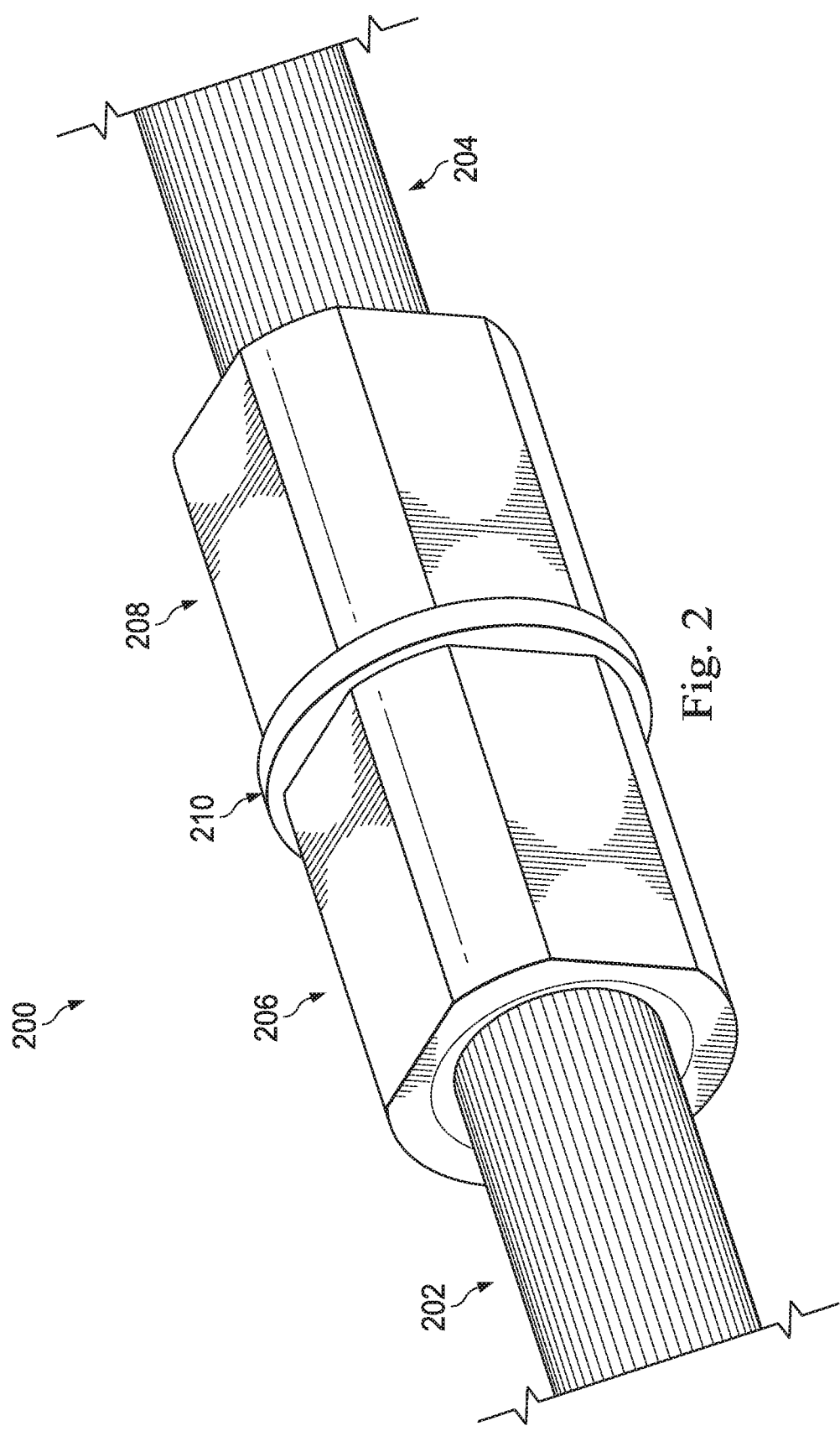

METHOD OF COUPLING OPTICAL FIBER BUNDLES

RELATED APPLICATIONS

This patent application claims priority to and the benefit of the filing date of U.S. Provisional Patent Application 62/529,040, entitled "Method of Coupling Optical Fiber Bundles," filed Jul. 6, 2017, which is incorporated by reference herein in its entirety.

FIELD

The present disclosure is directed to medical devices and methods for manufacturing medical devices. More particularly, the present disclosure is directed to coupling optical fiber bundles using systems and methods for interfacing the optical fibers in the optical fiber bundles.

BACKGROUND

Optical fiber bundles, which may also be referred to as fiber optic bundles, may be used in various applications that involve the transmission of light. An optical fiber bundle is an assembly of multiple optical fibers, each of which is capable of transmitting light from one end of the optical fiber to the other end. Many different types of medical instruments use optical fiber bundles for illumination, imaging, or both. An endoscope is one example of a medical instrument that uses optical fiber bundles. For example, an endoscope may be used to look inside the body at a particular internal organ. The endoscope may include one or more optical fiber bundles that are used for directing light towards the internal organ. The endoscope may also include one or more optical fiber bundles for capturing and carry an image of the internal organ to an eyepiece or some other type of image viewer.

In some optical devices, two or more optical fiber bundles may need to be coupled end-to-end. Ferrules are typically used for this type of coupling. However, currently available ferrules may not provide the desired interfacing percentage. The interfacing percentage indicates, for example, how well the optical fibers in a first optical fiber bundle overlap (i.e., match end to end) with the optical fibers in a second optical fiber bundle when the first and second optical fiber bundles are coupled together. A lower interfacing percentage may result in the loss of light that is conveyed between the two optical fiber bundles. Accordingly, more powerful light sources may be needed to account for the loss of light. These more powerful light sources may generate an undesired amount of heat at the location where the two optical fiber bundles are coupled. Thus, more efficient systems and methods for terminating optical fiber bundles are desirable.

SUMMARY

The embodiments of the invention are summarized by the claims that follow below.

In one illustrative embodiment, a method is provided. A plurality of fibers may be secured within a channel of a fastener system to place the plurality of fibers in a packing configuration within the channel. The fastener system and the plurality of fibers secured by the fastener system are cut through to create a first fiber bundle and a second fiber bundle. The first fiber bundle is coupled with the second fiber bundle.

In another illustrative embodiment, an apparatus comprises a fastener system that is separable to form a first fastener for a first fiber bundle and a second fastener for a second fiber bundle. The fastener system comprises a channel and a surface feature. The channel is configured to receive a plurality of fibers and that is shaped to place the plurality of fibers in a packing configuration. The surface feature is on an outer surface of the fastener system for use in forming a first set of alignment features on the first fastener and a second set of alignment features on the second fastener.

In yet another illustrative embodiment, a method is provided. A first fastener part and a second fastener part are positioned around an end portion of a fiber bundle. The first fastener part and the second fastener part are coupled to form a fastener system having a channel with a hexagonal cross-section. Coupling the first fastener part and the second fastener part places a plurality of fibers in the fiber bundle into a hexagonal packing configuration (i.e. a hex close packed configuration) within the channel. The fastener system is secured to the end portion of the fiber bundle using a binding material.

In still yet another illustrative embodiment, an apparatus comprises a first fastener part having a first set of mating features and a second fastener part having a second set of mating features. Coupling the first set of mating features with the second set of mating features forms a fastener having a channel with a hexagonal cross-section. The channel is configured to receive a plurality of fibers and place the plurality of fibers in a hexagonal packing configuration.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is an illustration of an enlarged view of a portion of an optical apparatus in accordance with an illustrative embodiment;

DETAILED DESCRIPTION

Figure 1A:
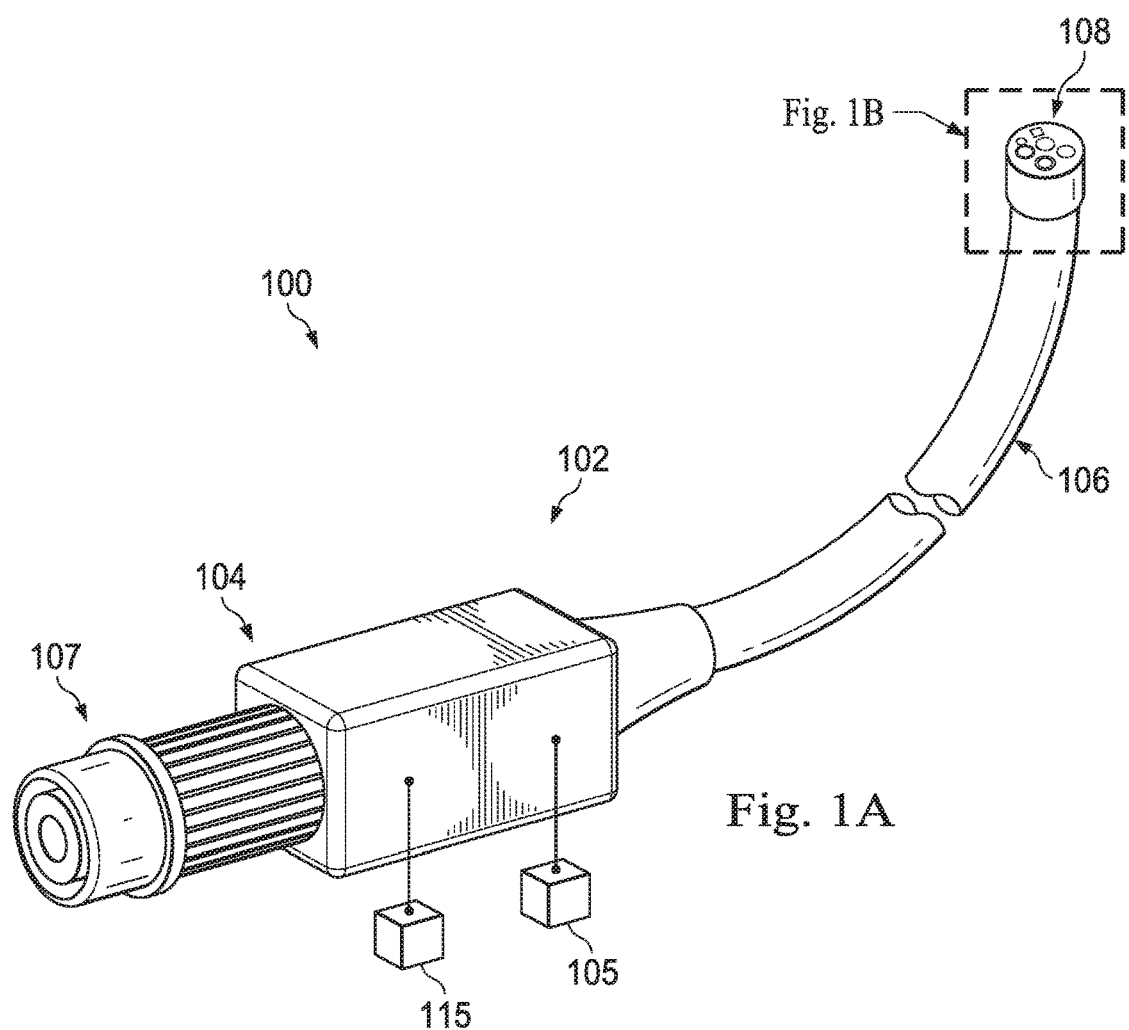
FIG. 1A is an illustration of a medical instrument in accordance with an illustrative embodiment.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

The illustrative embodiments described below provide a method and apparatus for coupling fiber bundles. In one illustrative embodiment, a plurality of fibers may be secured within a channel of a fastener system. In some cases, the channel may be shaped to place the plurality of fibers in a packing configuration within the channel. The packing configuration of a plurality of fibers is the shape of the cross-section of the fiber array. The packing configuration may be, for example, hexagonal, square or circular. A hexagonal packing configuration (i.e. a hex close packed configuration) may provide the highest packing density for the plurality of fibers.

Cutting through, or otherwise separating, the fastener system and the plurality of fibers secured by the fastener system may create a first fiber bundle and a second fiber bundle. The first fiber bundle may then be coupled with the second fiber bundle. One fiber bundle may be used as an input fiber bundle and the other fiber bundle used as the output fiber bundle. When the two fiber bundles are coupled, light may be sent through input fibers of the input fiber bundle, exit the input fibers, and enter the corresponding mating output fibers in the output fiber bundle. Cutting through the fastener system to create the first fiber bundle and the second fiber bundle ensures that the end portions of the first fiber bundle and the second fiber bundle have matching packing configurations. Accordingly, coupling these two separated fiber bundles may result in improved end-to-end matching or interfacing of the individual fibers, creating an improved interfacing percentage for the coupled fiber bundles as compared to coupling two independently created fiber bundles.

In particular, the process of packing the fibers within the fastener system, creating the two separated fiber bundles, and then coupling the two separated fiber bundles as described above may improve the packing density of the fibers in each fiber bundle, reduce the lateral offset between the input fibers and the mating output fibers, and match optical axis angles between the input fibers and the mating output fibers. In this manner, the coupling efficiency may be improved and illumination losses may be reduced. The coupling efficiency may be the percentage of the light captured by the output fibers from the light that exits the input fibers. The coupling efficiency may be, for example, greater than about 50 percent. In some instances, the coupling efficiency may be between about 50 percent and about 80 percent. The illumination losses may be reduced to, for example, a range between about −1 decibel (dB) and about −3 decibels (dB).

The illustrative embodiments also provide a method and apparatus for coupling fiber bundles using a multi-part fastener system. In one illustrative embodiment, a first fastener part and a second fastener part are shaped such that when coupled together, the first fastener part and the second fastener part form a fastener system with a channel that has a hexagonally-shaped cross-section to encourage a hexagonal packing configuration. The first fastener part and the second fastener part may be positioned around a first end portion of a first fiber bundle and a second end portion of a second fiber bundle, respectively. The first fastener part and the second fastener part may then be secured together to form a fastener system that places a first plurality of fibers in the first fiber bundle in a first packing configuration and a second plurality of fibers in the second fiber bundle in a second packing configuration. The first and second packing configurations may match within selected tolerances to provide an improved interfacing percentage for the coupled fiber bundles.

Figure 1B:
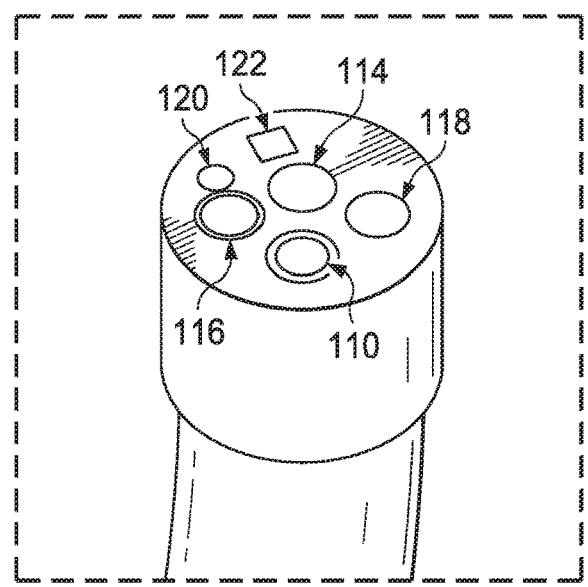
FIG. 1B is an illustration of a distal end of the medical instrument of FIG. 1A.

Referring to FIGS. 1A and 1B of the drawings, a medical instrument 100 is depicted in accordance with an illustrative embodiment. In this illustrative embodiment, the medical instrument 100 is an image capture device 102 that may be used to medically inspect various internal body parts and cavities. For example, the image capture device 102 may take the form of an endoscope used to capture images that can then be viewed by a human operator using the image capture device 102.

In one illustrative embodiment, the image capture device 102 may include a body 104, a light source 105, an elongated member 106, an eyepiece 107, and an image recording device 109. The body 104 is typically kept outside of the patient anatomy during the actual inspection. The elongated member 106 may be at least partially inserted inside the body such that a distal end 108 of the elongated member 106 is positioned relative to a body part of interest. The elongated member 106 may be rigid, flexible, articulated, partially flexible, or a combination thereof. Depending on the implementation, the elongated member 106 may be comprised of metal, plastic, a combination of the two, or some other suitable material.

The elongated member 106 may include channels housing various components, which may include an illumination system 110. The illumination system 110 may direct light from the light source 105 to illuminate the portion of the patient anatomy being inspected. In other words, the illumination system 110 may direct light towards the portion of the patient anatomy at which the distal end 108 of the elongated member 106 is pointing. In this illustrative embodiment, the illumination system 110 may include a light guide. In other embodiments, the illumination system 110 may include multiple light guides, one or more other components, or a combination thereof.

The elongated member 106 may also house an imaging bundle 114. The imaging bundle 114 may include a fiber bundle that is used to capture and convey an image to the image recording device 109 or to the eyepiece 107 for viewing by the human operator. The fiber bundle may be, for example, an optical fiber bundle comprised of a plurality of optical fibers. The image recording device 109 may take the form of a camera or some other type of image recording device.

Additionally, the elongated member 106 may house other components, such as, for example, without limitation, an air tube 116, a water tube 118, a suction tube 120, a control wire 122, or a combination thereof. In other illustrative embodiments, the elongated member 106 may also house some other type of component, such as, for example, a biopsy extraction device (not shown).

FIG. 2 is an illustration of an enlarged view of a portion of an optical apparatus 200, depicted in accordance with an illustrative embodiment. The optical apparatus 200 may be, for example, the illumination system 110 (e.g. the light guide) or the imaging bundle 114 in FIG. 1A. The optical apparatus 200 may extend within a channel of the elongated member 106 in FIG. 1A. In some illustrative embodiments, the optical apparatus 200 may be housed within a housing that extends within a channel of the elongated member 106.

In this illustrative embodiment, the optical apparatus 200 includes a first fiber bundle 202, a second fiber bundle 204, a first fastener 206, a second fastener 208, and a connector 210. The first fastener 206 is secured to the first fiber bundle 202. The second fastener 208 is secured to the second fiber bundle 204. The first fastener 206 and the second fastener 208 are coupled together by the connector 210 such that the first fiber bundle 202 is coupled to the second fiber bundle 204.

In this illustrative embodiment, the first fastener 206 and the second fastener 208 were created from a single fastener system, and the first fiber bundle 202 and the second fiber bundle 204 were created from a single original fiber bundle. Accordingly, coupling the first fastener 206 and the second fastener 208 to couple the first fiber bundle 202 and the second fiber bundle 204 may allow an increased overlap of fibers from the first fiber bundle 202 with the fibers in the second fiber bundle 204. Thus, the first fiber bundle 202 and the second fiber bundle 204 may have an improved interfacing percentage, which may, in turn, lead to reduced illumination losses.

Figure 3:
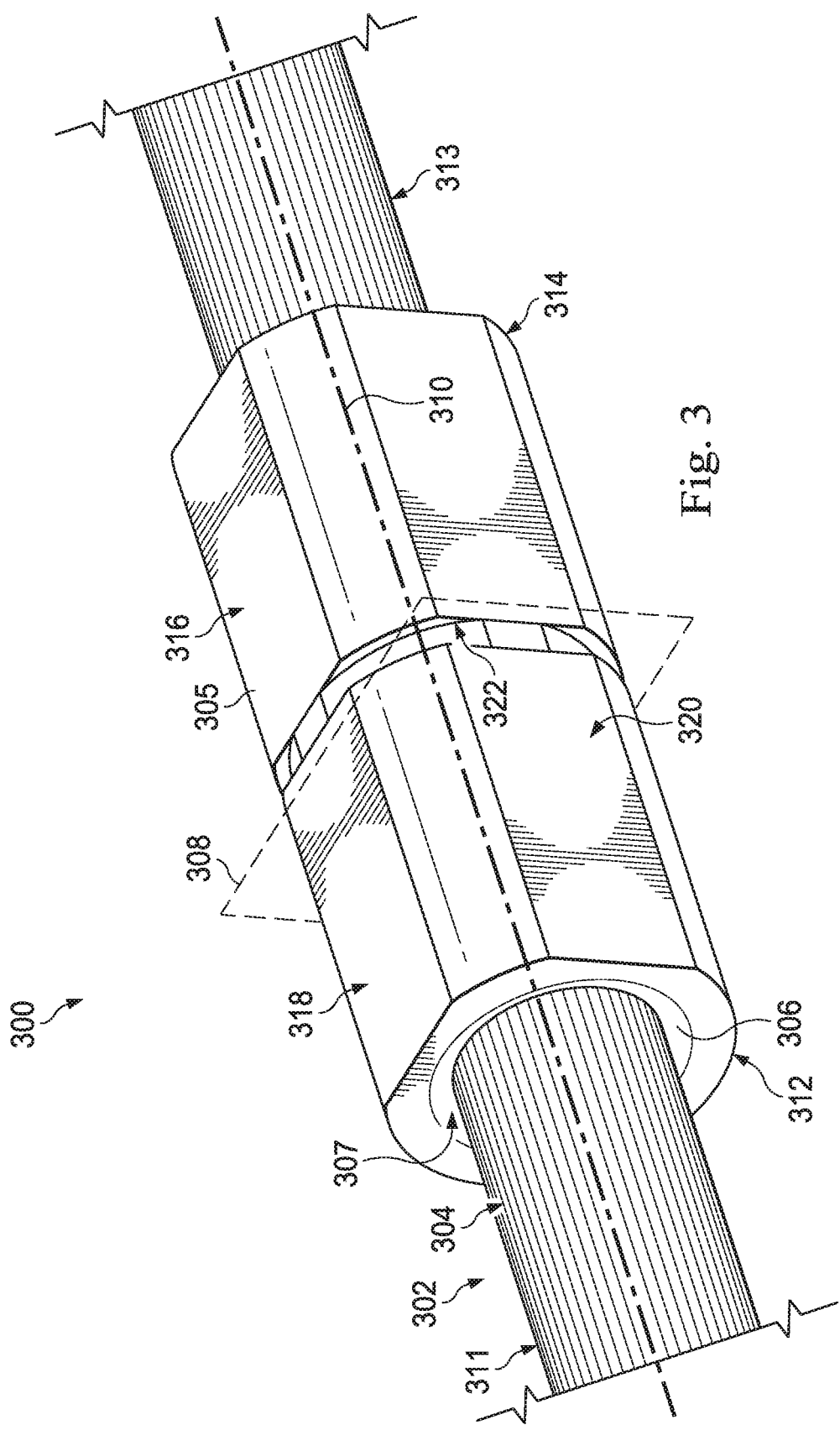
FIG. 3 is an illustration of a fastener system secured to a fiber bundle in accordance with an illustrative embodiment.

FIG. 3 is an illustration of a fastener system 300 secured to a fiber bundle 302, depicted in accordance with an illustrative embodiment. The fastener system 300 may be used to create the first fastener 206 and the second fastener 208 in FIG. 2. The fiber bundle 302 may be the original fiber bundle used to create the first fiber bundle 202 and the second fiber bundle 204 in FIG. 2.

As depicted, the fiber bundle 302 may be comprised of a plurality of fibers 304. The plurality of fibers 304 may be a plurality of optical fibers. Accordingly, the fiber bundle 302 may also be referred to as an optical fiber bundle or a fiber optic bundle.

In this illustrative embodiment, the fastener system 300 may take the form of a ferrule. As depicted, the ferrule may have a cylindrical-type shape. In other embodiments, the ferrule may have some other type of shape. The fastener system 300 has an outer surface 305 and an inner surface 306. The inner surface 306 defines a channel 307 through which the fiber bundle 302 is threaded.

In one illustrative embodiment, the channel 307 has a circular cross-section with respect to the plane 308 that extends approximately normal to the longitudinal axis 310 through the channel 307. The longitudinal axis 310 may be a center axis through the channel 307 of the fastener system 300.

The fastener system 300 has been positioned around the plurality of fibers 304 such that a first portion 311 of the plurality of fibers 304 extends past a first edge 312 of the fastener system 300 and a second portion 313 of the plurality of fibers 304 extends past a second edge 314 of the fastener system 300. In particular, the fastener system 300 may be positioned around the plurality of fibers 304 to ensure that the first portion 311 of the plurality of fibers 304 has a length sufficient to form the first fiber bundle 202 in FIG. 2 and that the second portion 313 of the plurality of fibers 304 has a length sufficient to form the second fiber bundle 204 in FIG. 2. In some cases, the first portion 311 and the second portion 313 may have the same length.

An adhesive (not shown) may be applied to secure the fiber bundle 302 within the fastener system 300. For example, without limitation, an adhesive may be injected between and around the plurality of fibers 304 within the channel 307 of the fastener system 300 such that the adhesive coats at least the portion of the plurality of fibers 304 and the inner surface 306 of the fastener system 300. The adhesive may then be cured. Depending on the implementation, various types of adhesive material may be used. In one illustrative embodiment, the adhesive may have a high glass-like durometer. The durometer may be a measurement of the hardness of the adhesive once the adhesive is cured. Further, the adhesive may be optically clear.

The outer surface 305 of the fastener system 300 may have a set of surface features 318, 320. The set of surface features 318, 320 may include one or more surface features that may be used to help rotationally orient the fastener system 300 with respect to the axis 310. A surface feature may take the form of, for example, without limitation, a flat portion of the outer surface 305, a notch, a curved portion of the outer surface 305, a texture, a color, a marking, a label, or some other type of feature. In this illustrative embodiment, the set of surface features may include a surface feature 318 and a surface feature 320. The surface feature 318 may take the form of, for example, without limitation, a flat portion of the outer surface 305. Similarly, the surface feature 320 may take the form of, for example, without limitation, a flat portion of the outer surface 305.

Additionally, the fastener system 300 also includes a plurality of separation guides 322. The separation guides 322 may include one or more separation guides that help indicate where the fastener system 300 may be cut to separate the fastener system 300 into two pieces. A separation guide may take the form of, for example, without limitation, a notch, a groove, a channel, a marking, a texture, a label, a color, or some other type of guide or feature. In this illustrative embodiment, the separation guides 322 may include one or more grooves along the outer surface 305 of the fastener system 300 that are substantially parallel to the plane 308. In this manner, the separation guides 322 may help identify where the fastener system 300 may be cut axially into two halves.

Once the fastener system 300 has been cut along the separation guides 322 (e.g., in the plane 308 or a plane parallel thereto), the fastener system 300 is separated into the first fastener 206 and the second fastener 208 in FIG. 2. Further, cutting through the fastener system 300 and the plurality of fibers 304 secured to the fastener system 300 separates the first portion 311 of the plurality of fibers 304 from the second portion 313. Accordingly, the first portion 311 becomes the first fiber bundle 202 and the second portion 313 of the plurality of fibers 304 becomes the second fiber bundle 204.

Figure 4:
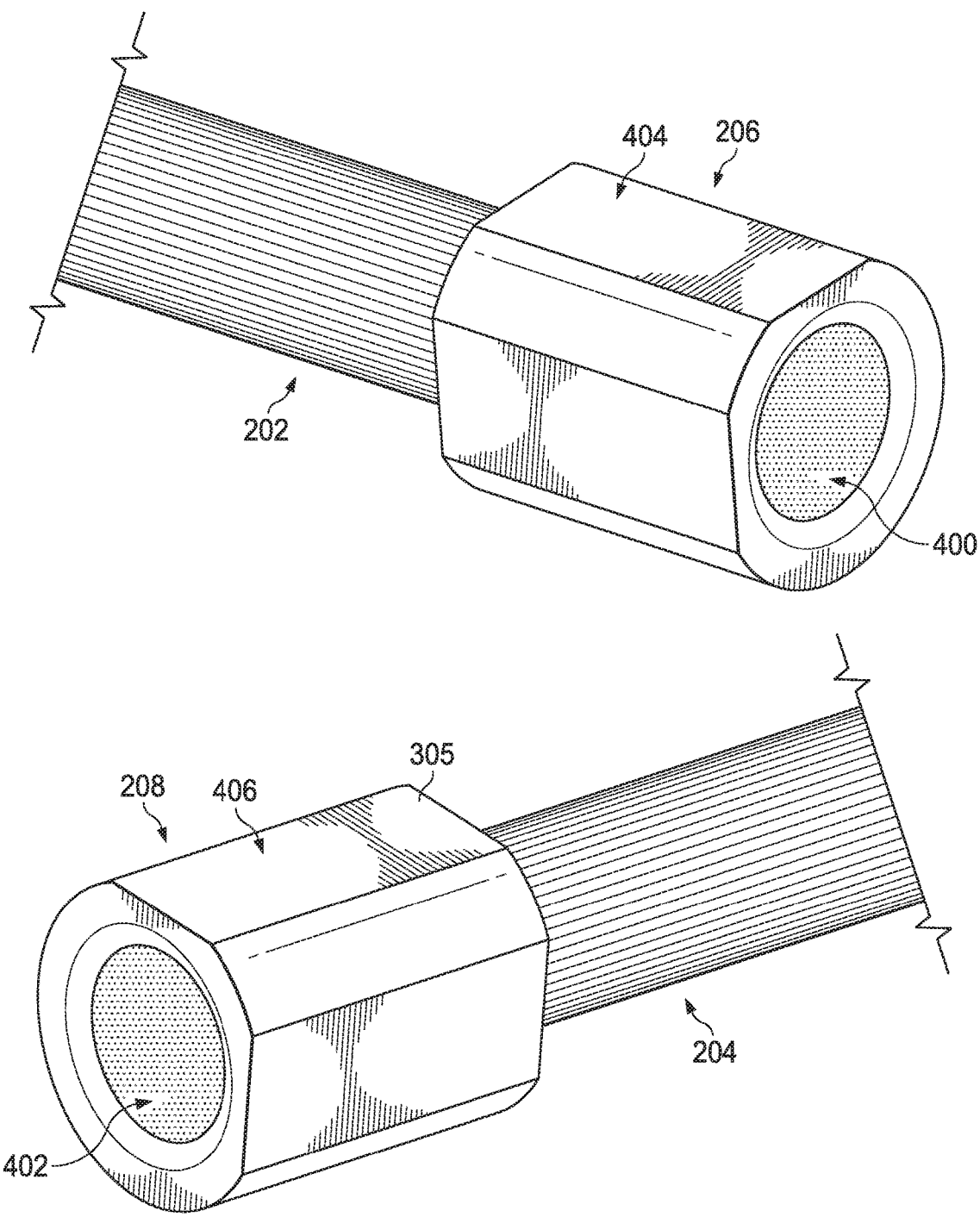
FIG. 4 is an illustration of a first fiber bundle secured to a first fastener and a second fiber bundle secured to a second fastener in accordance with an illustrative embodiment.

FIG. 4 is an illustration of the fiber bundle 202 secured to the first fastener 206 and the second fiber bundle 204 secured to the second fastener 208. In this illustrative example, the fastener system 300 shown in FIG. 3 has been cut along the separation guides 322 to form the first fastener 206 secured to the first fiber bundle 202 and the second fastener 208 secured to the second fiber bundle 204.

As depicted, the first fiber bundle 202 may have a first exposed end 400, and the second fiber bundle 204 may have a second exposed end 402. Adhesive and the fiber ends from where the plurality of fibers 304 in FIG. 3 was cut may be exposed at both the first exposed end 400 and the second exposed end 402. In some illustrative embodiments, the first exposed end 400 and the second exposed end 402 may be polished to improve the optical quality of the fiber ends and maximize the conveyance of light from fiber to fiber when the first fiber bundle 202 is coupled with the second fiber bundle 204.

In this illustrative embodiment, the first fastener 206 has an alignment feature 404 and the second fastener 208 has an alignment feature 406. The alignment features 404, 406 are formed from the surface feature 318 in FIG. 3 when the fastener system 300 is cut into two pieces.

The alignment feature 404 and the alignment feature 406 may be used to help align the first fastener 206 and the second fastener 208 relative to each other. As one illustrative example, the alignment feature 404 and the alignment feature 406 may be used to position the first fastener 206 and the second fastener 208, respectively, relative to an assembly apparatus (not shown) that is used to couple these two fasteners together. The assembly apparatus may take the form of, for example, without limitation, a jig that is used to control the location and motion of the first fastener 206 and the second fastener 208 during coupling.

Aligning the first fastener 206 and the second fastener 208 together may ensure that the individual fibers of the first fiber bundle 202 and the individual fibers of the second fiber bundle 204 also align within selected tolerances. Accordingly, the percentage of the fibers in the first fiber bundle 202 that interface with the fibers in the second fiber bundle 204 when the two fiber bundles are coupled may be improved, thereby helping reduce future illumination losses.

Figure 5:
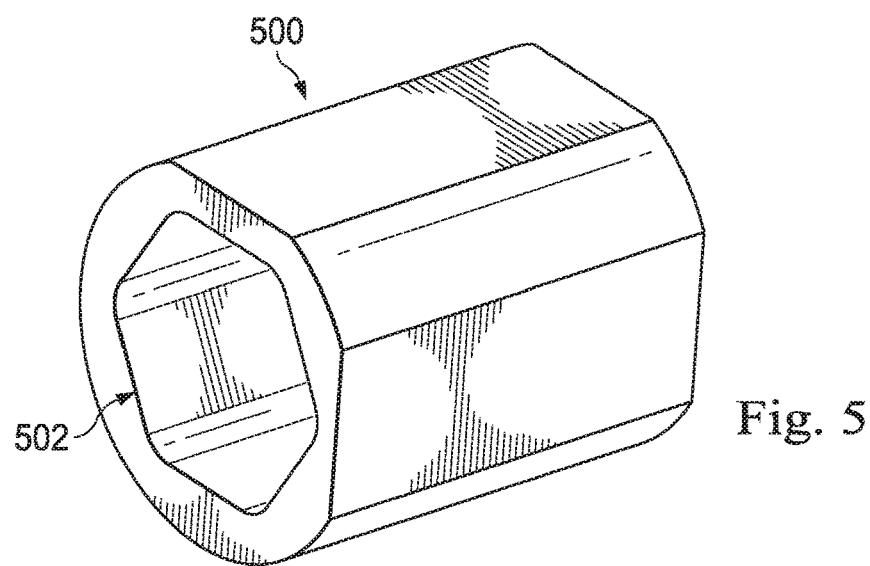
FIG. 5 is an illustration of another fastener system having an alternative channel cross-sectional shape in accordance with an illustrative embodiment.

FIG. 5 is an illustration of fastener system 500, similar to fastener system 300 having a channel 502 shaped differently than the channel 307 in FIG. 3. In this illustrative embodiment, the fastener system 500 has a channel 502, which has a hexagonal cross-section in a plane normal to a longitudinal axis through the channel 502.

This type of fastener system 500 having the channel 502 may allow the plurality of fibers 304 of the fiber bundle 302 from FIG. 3 to be placed in a hexagonal packing configuration when passed through the channel 502. The hexagonal packing configuration may have a higher packing efficiency than the circular packing configuration achieved by the circular cross-section of the channel 307 in FIG. 3. For example, the hexagonal packing configuration may have a packing efficiency of between about 85 and about 95 percent. The improved packing efficiency may help increase the interfacing percentage, and thereby reduce future illumination losses.

Figure 6:
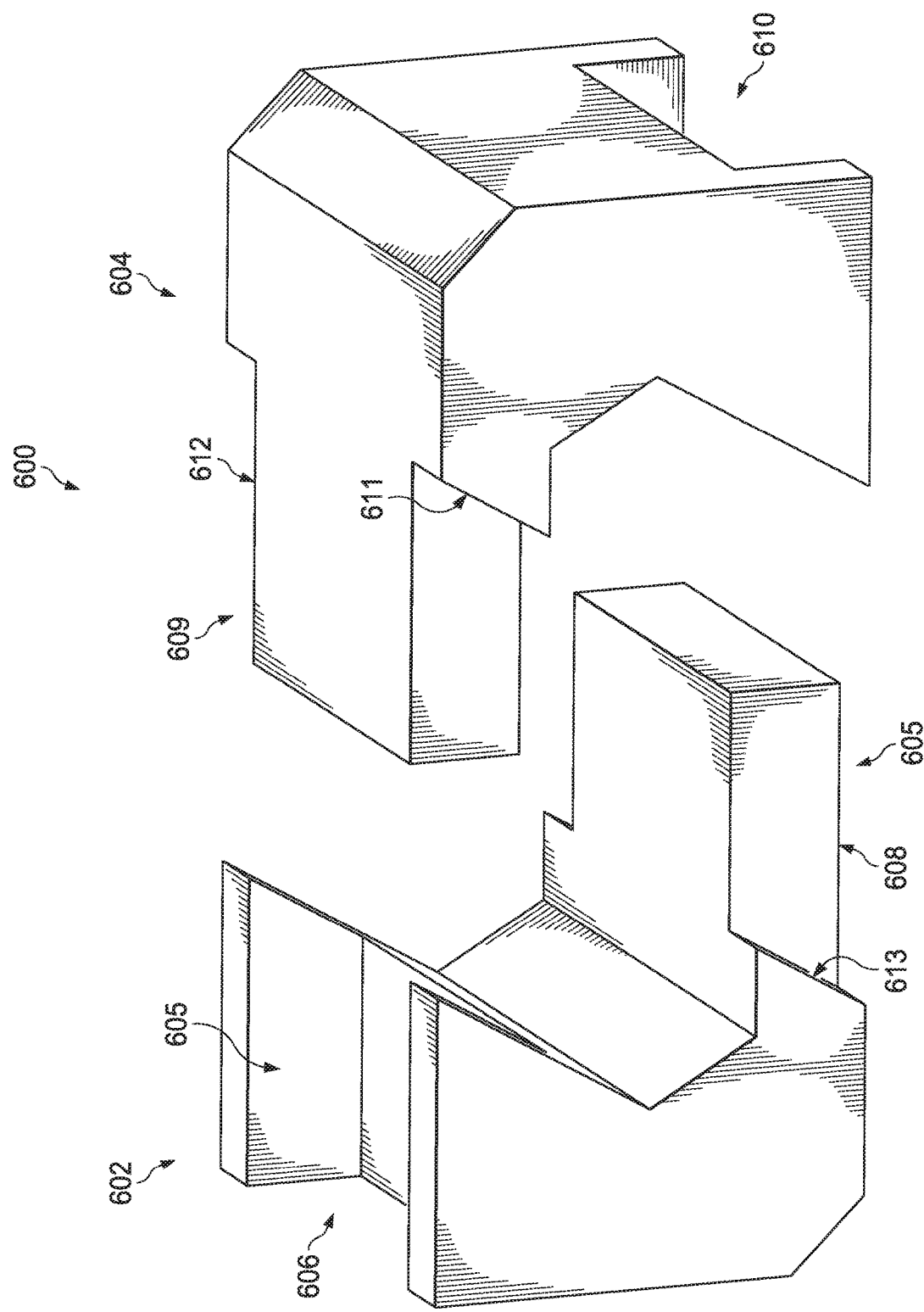
FIG. 6 is an illustration of two parts of a fastener in accordance with an illustrative embodiment.

FIG. 6 is an illustration of two parts of a fastener 600, depicted in accordance with an illustrative embodiment. As depicted, the fastener 600 includes a first fastener part 602 and a second fastener part 604. The first part 602 and the second part 604 are shaped such that when the first part 602 and the second part 604 are coupled together, the first part 602 and the second part 604 form a channel having a cross-section that is hexagonally shaped.

The first part 602 may have a first set of mating features 605 that is configured to engage with a second set of mating features 609 on the second part 602. In one illustrative embodiment, the first set of mating features 605 may include a first channel 606 and a first protruding feature 608. The second set of mating features 609 may include a second channel 610 and a second protruding feature 612. The first channel 606 and the second protruding feature 612 may be shaped to engage with each other such that the protruding feature slides within the channel until the first fastener part 602 contacts an abutment surface 611 of the second part 604. The second channel 610 and the first protruding feature 608 may be shaped to engage with each other such that the protruding feature slides within the channel until the second fastener part 604 contacts an abutment surface 613 of the first part 604.

Figure 7:
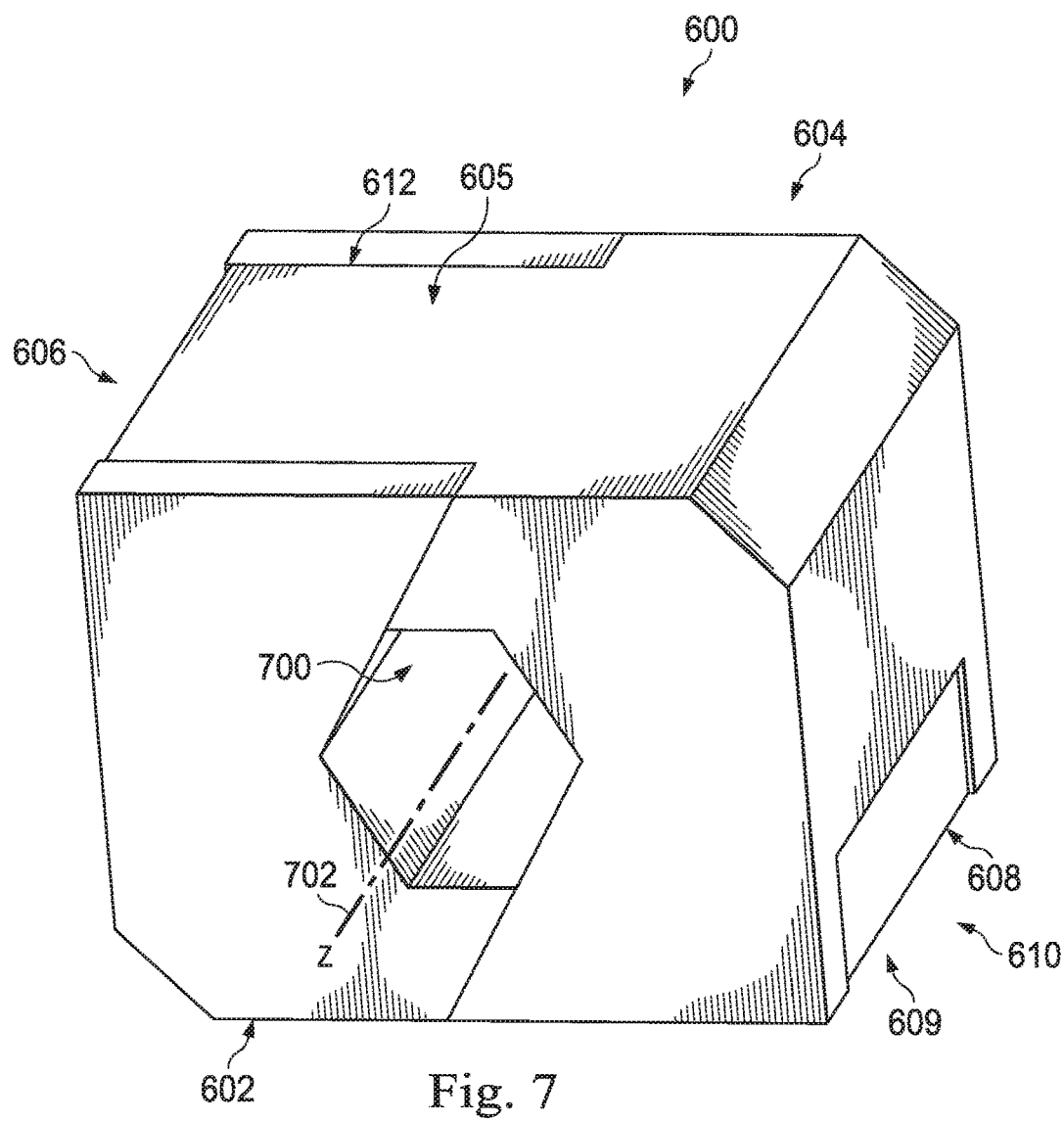
FIG. 7 is an illustration of the fastener of FIG. 6 coupled together in accordance with an illustrative embodiment.

FIG. 7 is an illustration of the first part 602 and the second part 604 of the fastener 600 coupled together, depicted in accordance with an illustrative embodiment. The first protruding feature 608 of the first part 602 has been engaged with the second channel 610 of the second part 604 and the second protruding feature 612 of the second part 604 has been engaged with the first channel 606 of the first part 602.

As depicted, when the first part 602 and the second part 604 are coupled, the fastener 600 forms a channel 700. In this example, the channel 700 has a hexagonal cross-section with respect to a plane (not shown) that is normal to the longitudinal axis 702. The axis 702 may be a center axis through the channel 700 of the fastener 600.

Figure 8:
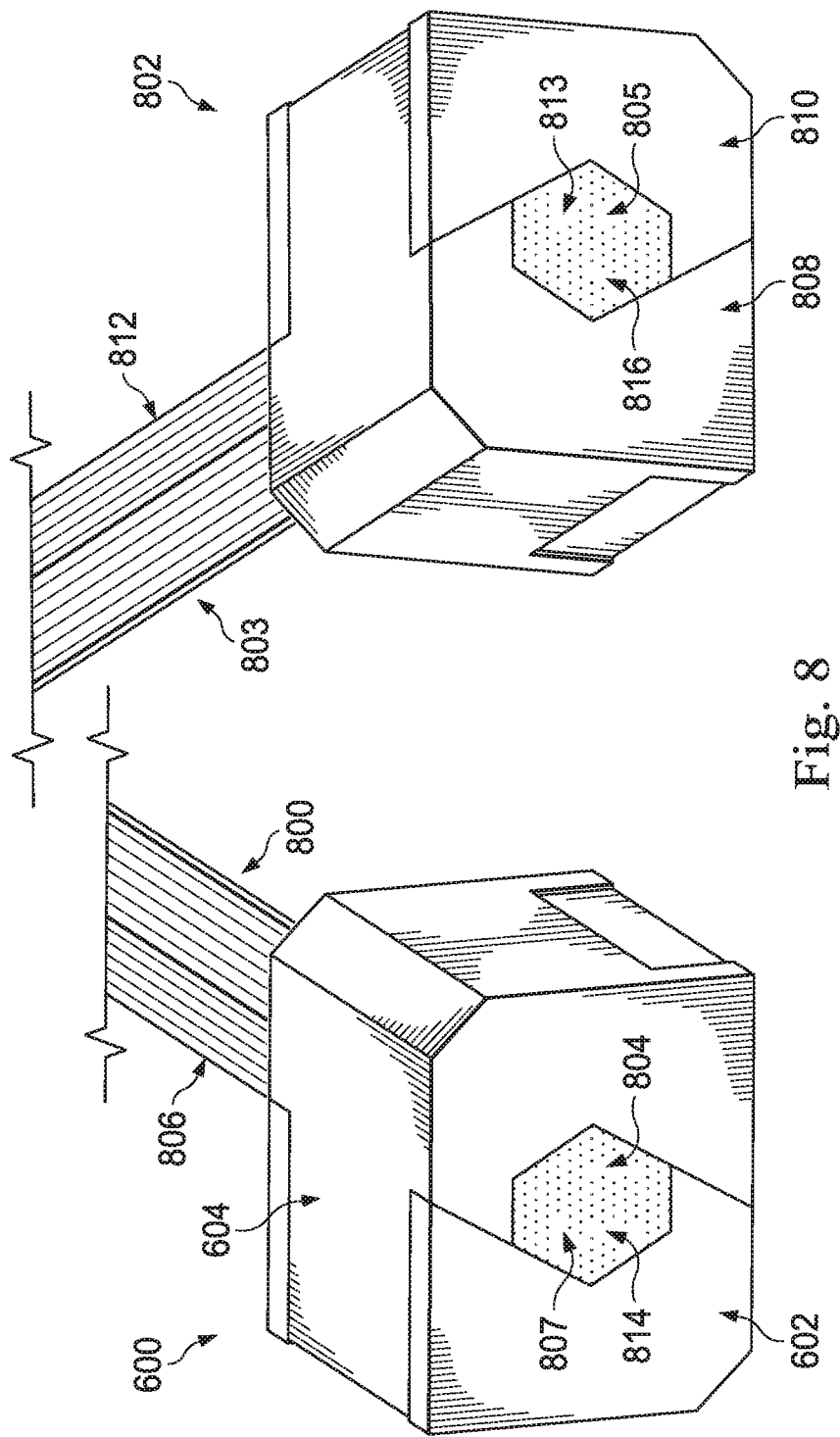
FIG. 8 is an illustration of a fastener secured to a first fiber bundle and another fastener secured to a second fiber bundle in accordance with an illustrative embodiment.

FIG. 8 is an illustration of the fastener 600 secured to a first fiber bundle 800 and another fastener 802 secured to a second fiber bundle 803, depicted in accordance with an illustrative embodiment. The fastener 600 has been secured to an end portion 804 of the first fiber bundle 800. The fastener 802 has been secured to an end portion 805 of the second fiber bundle 803.

For example, without limitation, the first part 602 of the fastener 600 and the second part 604 of the fastener 600 may be positioned around the end portion 804 of the first fiber bundle 800 and then mated. Mating the first part 602 and the second part 604 together around the first fiber bundle 800 places a first plurality of fibers 806 in the first fiber bundle 800 in a hexagonal packing configuration. For example, the first part 602 and the second part 604 may be used to clamp the first plurality of fibers 806 radially to place the first plurality of fibers 806 in the hexagonal packing configuration. An adhesive 807 may be applied to the end portion 804 of the first fiber bundle 800 within the fastener 600 and then cured to secure the fastener 600 to the first fiber bundle 800.

In a similar manner, a third part 808 and a fourth part 810 may be positioned around the end portion 805 of the second fiber bundle 803 and then mated to form the fastener 802.

Mating the third part 808 and the fourth part 810 together around the second fiber bundle 803 places a second plurality of fibers 812 in the second fiber bundle 803 in a hexagonal packing configuration. For example, the third part 808 and the fourth part 810 may be used to clamp the second plurality of fibers 812 radially to place the second plurality of fibers 812 in a similar hexagonal packing configuration as the hexagonal packing configuration for the first plurality of fibers 806. An adhesive 813 may be applied to the end portion 805 of the second fiber bundle 803 and then cured to secure the fastener 802 to the second fiber bundle 803.

The first fiber bundle 800 has a first exposed end 814 at which fiber ends and the adhesive 807 are exposed. The second fiber bundle 802 has a second exposed end 816 at which the fiber ends and the adhesive 813 are exposed. The first exposed end 814 and the second exposed end 816 may be polished down to improve an optical quality of the fiber ends and maximize the conveyance of light from fiber to fiber when the first fiber bundle 800 and the second fiber bundle 803 are coupled.

The fastener 600 and the fastener 802 may be coupled together to thereby couple the first fiber bundle 800 and the second fiber bundle 803. In one illustrative embodiment, the fastener 600 and the fastener 802 may be coupled together in a manner similar to the coupling of the first fastener 206 and the second fastener 208 shown in FIG. 2.

Because the packing efficiency of the hexagonal packing configuration is high, variability between the hexagonal packing configuration of the first plurality of fibers 806 and of the second plurality of fibers 812 is reduced. Accordingly, the hexagonal packing configurations of the first fiber bundle 800 and the second fiber bundle 803 enable a greater number of fibers to interface end-to-end, thereby increasing the interfacing percentage.

In other illustrative embodiments, only a single fastener, such as the fastener 600, may be used to couple together the first fiber bundle 800 and the second fiber bundle 803. For example, the first fiber bundle 800 and the second fiber bundle 803 may be positioned relative to each other. In some cases, an adhesive may be applied around and between the first fiber bundle 800 and the second fiber bundle 803 to loosely hold these two fiber bundles together. Next, the first part 602 and the second part 604 may be positioned around the first fiber bundle 800 and the second fiber bundle 803 and then mated to couple the first fiber bundle 800 to the second fiber bundle 803 such that first fiber bundle extends within one end of the channel 700 and the second fiber bundle extends within the other end of the channel. In this manner, a single fastener may be used to couple together the first fiber bundle 800 and the second fiber bundle 803 within the channel 700.

Figure 9:
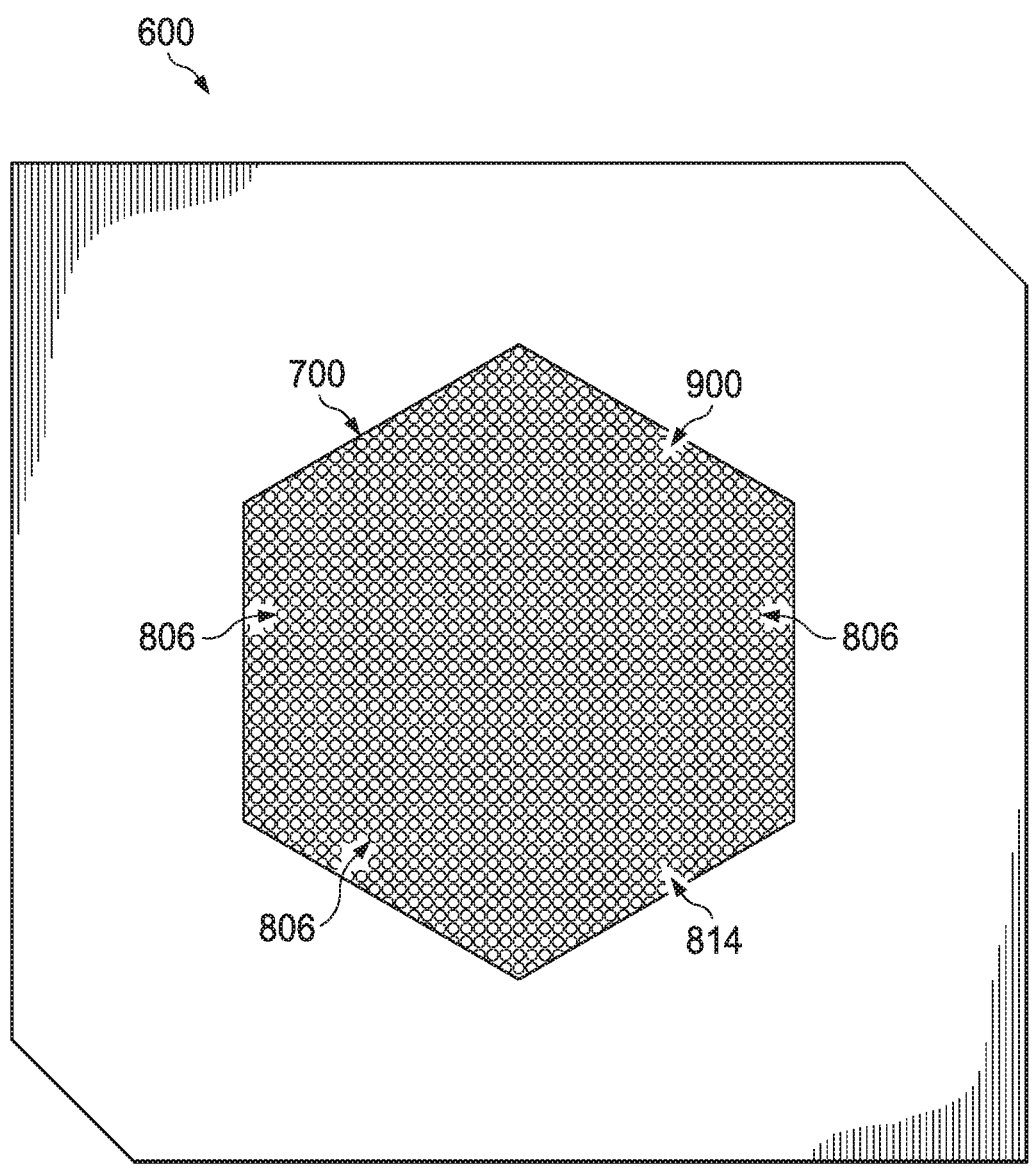
FIG. 9 is an illustration of an end view of a first exposed end of a first fiber bundle in accordance with an illustrative embodiment.

FIG. 9 is an illustration of an end view of the first exposed end 814 of the first fiber bundle 800, depicted in accordance with an illustrative embodiment. The plurality of fibers 806 has the hexagonal packing configuration 900. The high packing efficiency of the hexagonal packing configuration 900 may help ensure that coupling the first exposed end 814 of the first fiber bundle 800 to the second exposed end 816 of the second fiber bundle 803, which has a similar hexagonal packing configuration, may result in an increased interfacing percentage. A higher interfacing percentage helps reduce loss of light when light is conveyed from the fibers of one fiber bundle to the fibers of the other.

The illustrations in FIGS. 1-9 are not meant to imply physical or architectural limitations to the manner in which the different illustrative embodiments may be implemented. Other components in addition to or in place of the ones illustrated may be used. Some components may be optional.

For example, in some illustrative embodiments, the fastener 600 may be formed by more than two parts. For example, three or four parts may be configured to be mated together to form the fastener 600. In other illustrative embodiments, a flexible material such as, for example, without limitation, a fabric-type material, a plastic mesh, a metallic mesh, or some other type of material, may be placed around the end portion 804 of the first fiber bundle 800 prior to the fastener 600 being secured to the end portion 804.

Figure 10:
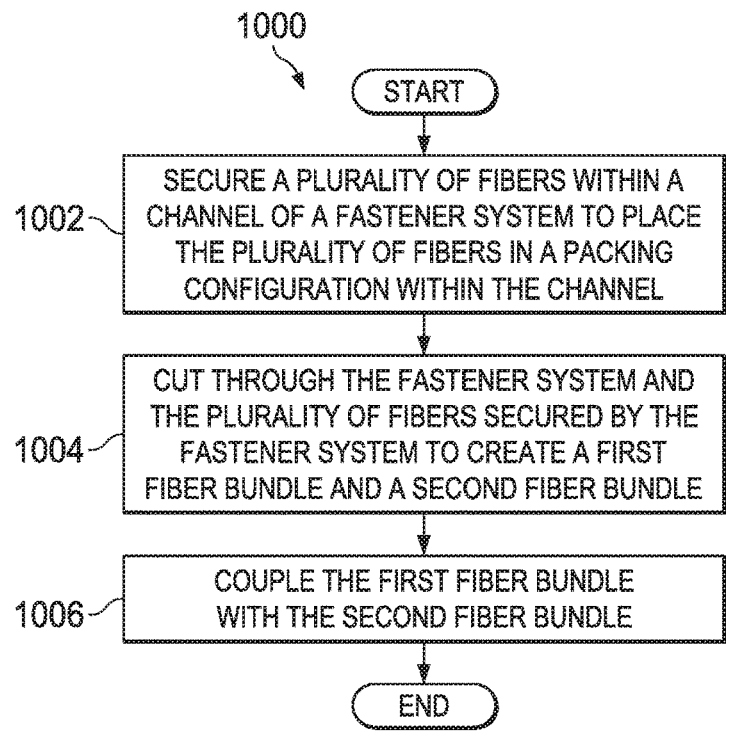
FIG. 10 is an illustration of a method for coupling fiber bundles in accordance with an illustrative embodiment.

FIG. 10 is an illustration of a method for coupling fiber bundles, depicted in accordance with an illustrative embodiment. The method 1000 illustrated in FIG. 10 may be used to couple together a first fiber bundle and a second fiber bundle, such as the first fiber bundle 202 and the second fiber bundle 204 described in previous figures. Although the fiber bundles may be coupled as previously illustrated, the method of this disclosure may be used (with or without polishing) to couple together fiber bundles within other optical fixtures. In some embodiments, more than two fiber bundles may be coupled together end-to-end using the method of this disclosure.

The method 1000 is illustrated as a set of operations or processes 1002-1006. Not all of the illustrated processes 1002-1006 may be performed in all embodiments of method 1000. Additionally, one or more processes that are not expressly illustrated in FIG. 10 may be included before, after, in between, or as part of the processes 1002-1006. In some embodiments, one or more of the processes 1002-1006 may be optional and therefore omitted.

The method 1000 may begin with a process 1002 that includes securing a plurality of fibers within a channel of a fastener system to place the plurality of fibers in a packing configuration within the channel. For example, the plurality of fibers may be threaded through the channel of the fastener system. In some embodiments, an adhesive may be used to further secure the fastener system to the plurality of fibers. In some embodiments the channel may have a hexagonal cross-section.

The process 1004 includes cutting through the fastener system and the plurality of fibers secured by the fastener system to create a first fiber bundle and a second fiber bundle. For example, in process 1004, cutting through the fastener system axially may separate the fastener system into a first fastener that remains secured to a first portion of the plurality of fibers and a second fastener that remains secured to a second portion of the plurality of fibers. The first portion may form the first fiber bundle and the second portion may form the second fiber bundle.

At process 1006, the first fiber bundle is coupled with the second fiber bundle, with the process terminating thereafter. In process 1006, because the first fiber bundle and the second fiber bundle were created from the same plurality of fibers with the plurality of fibers already in the same packing configuration, all or a large percentage of the fibers of these two fiber bundles may match up end-to-end, creating a high efficiency interface. This large interfacing percentage may lead to a reduction in the amount of light lost during the conveyance of light between the first fiber bundle and the second fiber bundle. This reduction in illumination losses may allow less powerful light sources to be used when using these coupled fiber bundles for illumination purposes. In some illustrative embodiments, process 1004 or process 1006 may optionally include polishing the cut ends of the first fiber bundle and the second fiber bundle prior to coupling these two fiber bundles. Polishing the cut ends of these fiber bundles may make the coupling process easier and improve the quality of the coupling. In other illustrative embodiments, the method 1000 may include a polishing process that is performed between process 1004 and process 1006.

Figure 11:
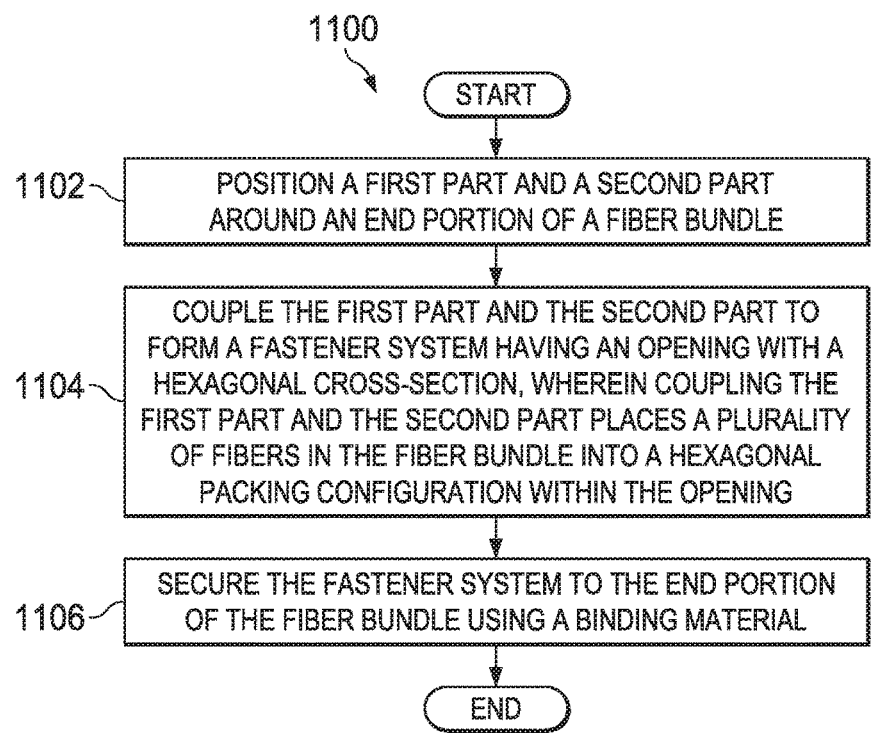
FIG. 11 is an illustration of a method for securing a fastener to a fiber bundle in accordance with an illustrative embodiment.

FIG. 11 is an illustration of a method for securing a fastener to a fiber bundle, depicted in accordance with an illustrative embodiment. The method 1100 illustrated in FIG. 11 may be used to couple together a first fiber bundle and a second fiber bundle, such as the first fiber bundle 800 and the second fiber bundle 803 described in previous figures. Although the fiber bundles may be coupled as previously illustrated, the method of this disclosure may be used (with or without polishing) to couple together fiber bundles within other optical fixtures. In some embodiments, more than two fiber bundles may be coupled together end-to-end using the method of this disclosure.

The method 1100 is illustrated as a set of operations or processes 1102-1106. Not all of the illustrated processes 1102-1106 may be performed in all embodiments of method 1100. Additionally, one or more processes that are not expressly illustrated in FIG. 11 may be included before, after, in between, or as part of the processes 1102-1106. In some embodiments, one or more of the processes 1102-1106 may be optional and therefore omitted.

The method may begin with a process 1102 that includes positioning a first part and a second part around an end portion of a fiber bundle. In process 1102, the first part may have a first set of mating features that are configured to engage with a second set of mating features of the second part.

At process 1104, the first part and the second part are coupled to form a fastener system (e.g. system 600) having a channel with a hexagonal cross-section, wherein coupling the first part and the second part places a plurality of fibers in the fiber bundle into a hexagonal packing configuration within the channel. In process 1104, coupling the first part and the second part together may include engaging the first set of mating features on the first part with the second set of mating features on the second part. Further, mating the first part and the second part may apply a clamping force that places the plurality of fibers into the hexagonal packing configuration. In this manner, the plurality of fibers may be clamped together radially.

At process 1106, a binding material is used to secure the fastener system to the end portion of the fiber bundle, with the process terminating thereafter. In process 1106, the binding material may take the form of an adhesive, a resin, a potting agent, or some other type of a binding agent. When the process 1006 includes using an adhesive, the adhesive may be, for example, injected between the plurality of fibers and the fastener system and then cured to secure the fastener system to the end portion of the fiber bundle.

Figure 12:
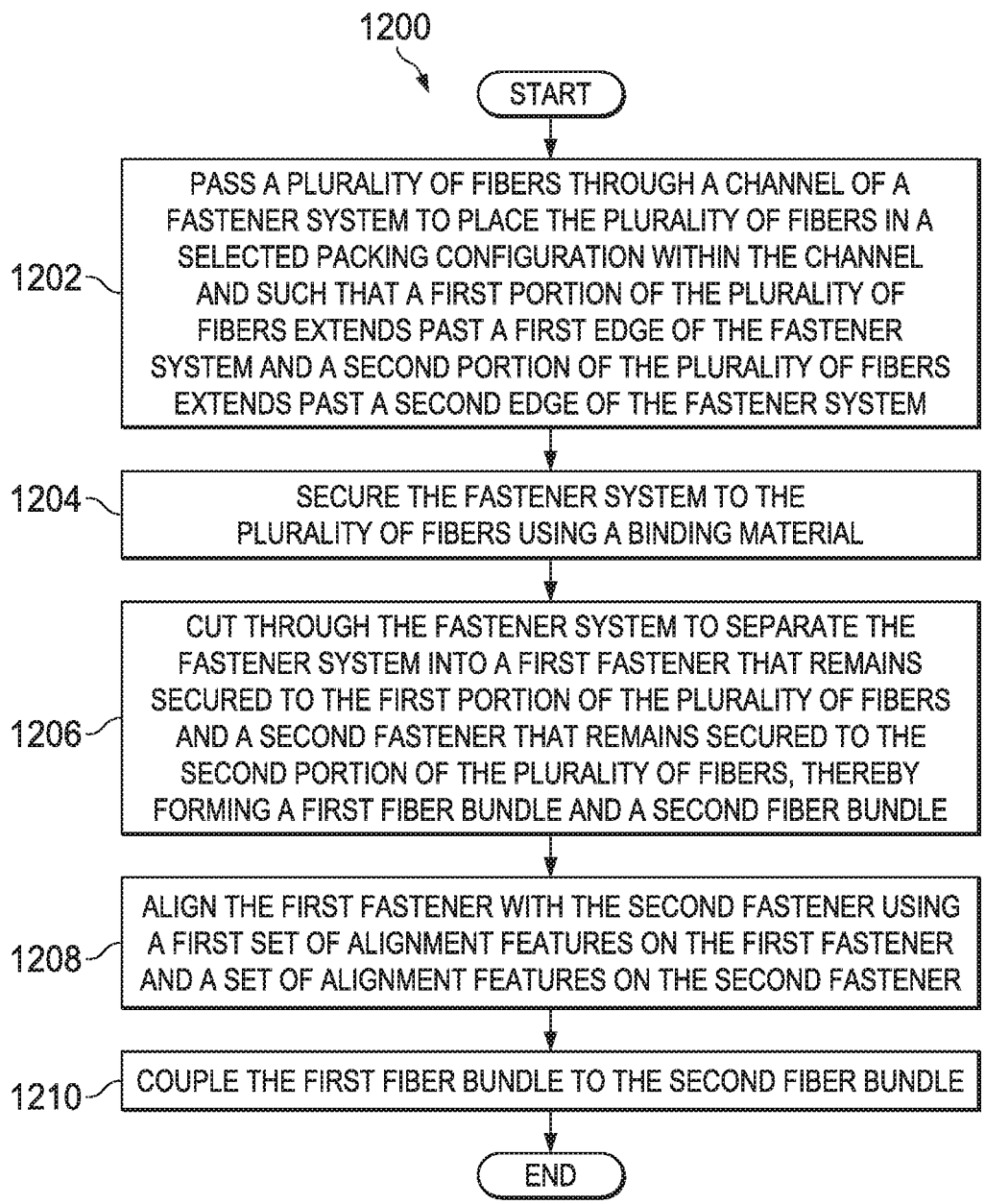
FIG. 12 is an illustration is an illustration of a method for coupling fiber bundles in accordance with an illustrative embodiment.

FIG. 12 is an illustration of a method for coupling fiber bundles, depicted in accordance with an illustrative embodiment. The method 1200 illustrated in FIG. 12 may be used to couple together a first fiber bundle and a second fiber bundle, such as the first fiber bundle 202 and the second fiber bundle 204 described in previous figures. The method 1200 is illustrated as a set of operations or processes 1202-1210. Not all of the illustrated processes 1202-1210 may be performed in all embodiments of method 1200. Additionally, one or more processes that are not expressly illustrated in FIG. 12 may be included before, after, in between, or as part of the processes 1202-1210. In some embodiments, one or more of the processes 1202-1210 may be optional and therefore omitted.

The method 1200 may begin with a process 1202 that includes passing a plurality of fibers through a channel of a fastener system to place the plurality of fibers in a selected packing configuration within the channel and such that a first portion of the plurality of fibers extends past a first edge of the fastener system and a second portion of the plurality of fibers extends past a second edge of the fastener system. In process 1202, the selected packing configuration may be a hexagonal packing configuration. But in other illustrative embodiments, the selected packing configuration may be a circular packing configuration, a square packing configuration, or some other type of packing configuration.

At process 1204, the fastener system is secured to the plurality of fibers using a binding material. In process 1204, the binding material may include at least one of an adhesive, a resin, a potting agent, or some other type of binding material or agent. When the process 1204 includes using an adhesive, the process 1204 may also include curing the adhesive. At process 1206, the fastener system is cut through axially to separate the fastener system into a first fastener that remains secured to the first portion of the plurality of fibers and a second fastener that remains secured to the second portion of the plurality of fibers, thereby forming a first fiber bundle and a second fiber bundle.

Then, at process 1208, the first fastener is aligned with the second fastener using a first set of alignment features on the first fastener and a set of alignment features on the second fastener. In process 1208, the first set of alignment features and the second set of alignment features may be formed when the fastener system is cut in the process 1206. These two sets of alignment features may be used to align the two fasteners to ensure that best match at an interface between the first fiber bundle and the second fiber bundle.

At process 1210, the first fiber bundle is coupled to the second fiber bundle such that a large percentage of the fibers are interfaced end-to-end, with the process terminating thereafter. This large interfacing percentage may help ensure a reduction in the loss of light conveyed between the two coupled fiber bundles. Accordingly, less powerful lights sources may be used to provide illumination through these coupled fiber bundles.

Figure 13:
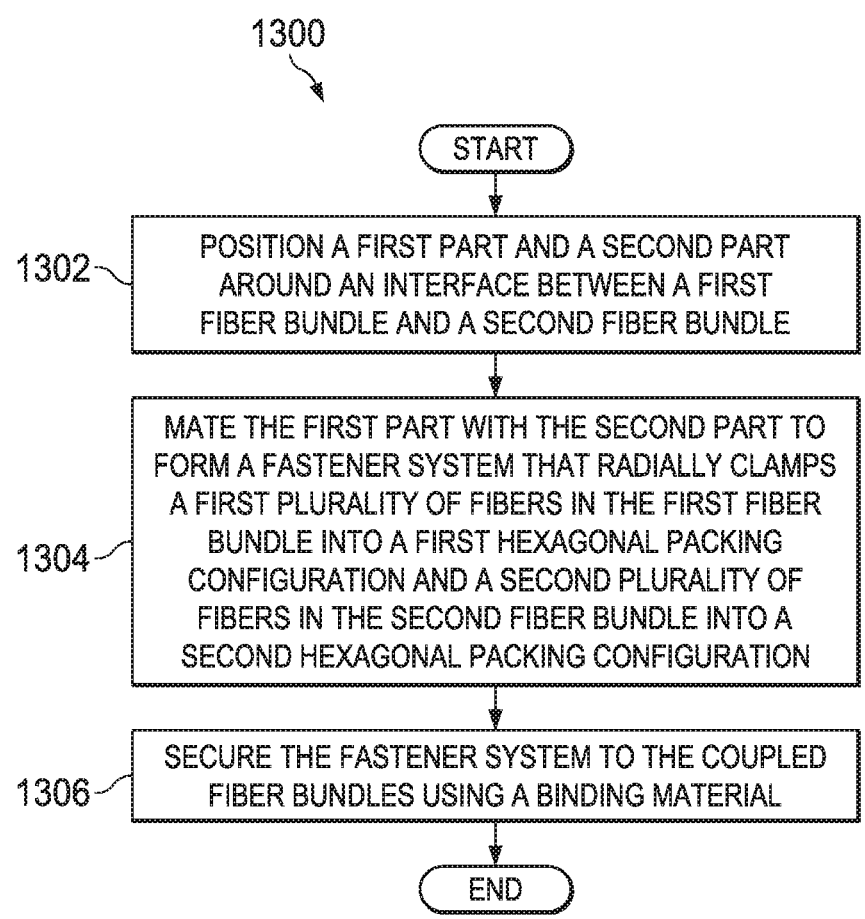
FIG. 13 is an illustration is an illustration of a method for coupling fiber bundles in accordance with an illustrative embodiment.

FIG. 13 is an illustration of a method for coupling fiber bundles, depicted in accordance with an illustrative embodiment. The method 1300 illustrated in FIG. 13 may be used to couple together a first fiber bundle and a second fiber bundle, such as the first fiber bundle 800 and the second fiber bundle 803 described in previous figures. The method 1300 is illustrated as a set of operations or processes 1302-1310. Not all of the illustrated processes 1302-1310 may be performed in all embodiments of method 1300. Additionally, one or more processes that are not expressly illustrated in FIG. 13 may be included before, after, in between, or as part of the processes 1302-1310. In some embodiments, one or more of the processes 1302-1310 may be optional and therefore omitted.

The method may begin with a process 1302 that includes positioning a first part and a second part around an interface between a first fiber bundle and a second fiber bundle. In process 1302, the interface may be between a first end portion of the first fiber bundle and a second end portion of the second fiber bundle.

At process 1304, the first part is mated with the second part to form a fastener system that radially clamps a first plurality of fibers in the first fiber bundle into a first hexagonal packing configuration and a second plurality of fibers in the second fiber bundle into a second hexagonal packing configuration. In process 1304, the variability between the first hexagonal packing configuration and the second hexagonal packing configuration may be sufficiently low such that the interfacing percentage between the first fiber bundle and the second fiber bundle is above a selected threshold.

Next, at process 1306, a binding material is used to bind the fastener system to the coupled fiber bundles, with the process terminating thereafter. The binding material may include at least one of an adhesive, a potting agent, a resin, or some other type of binding material or agent. If an adhesive is used, the process 1306 may include curing the adhesive.

While certain exemplary embodiments of the invention have been described and shown in the accompanying drawings, it is to be understood that such embodiments are merely illustrative of and not restrictive on the broad invention. Additionally, it is to be understood that the embodiments of the invention are not be limited to the specific constructions and arrangements shown and described, since various other modifications may occur to those ordinarily skilled in the art.

Further, in the detailed description of the embodiments of the invention, numerous specific details have been set forth in order to provide a thorough understanding of the disclosed embodiments. However, it will be obvious to one skilled in the art that the embodiments of this disclosure may be practiced without these specific details. In some instances, well known methods, procedures, and components have not been described in detail so as not to unnecessarily obscure aspects of the embodiments of the invention.

What is claimed is:

1. A method comprising:
   securing a plurality of fibers within a channel of a fastener system to place the plurality of fibers in a packing configuration within the channel;
   cutting through the fastener system and the plurality of fibers secured by the fastener system to create:
      a first fiber bundle and a second fiber bundle; and
      a first fastener coupled to the first fiber bundle and a second fastener coupled to the second fiber bundle; and
   coupling the first fiber bundle with the second fiber bundle, wherein coupling the first fiber bundle with the second fiber bundle comprises coupling the first fastener with the second fastener.

2. The method of claim 1, wherein securing the plurality of fibers within the channel of the fastener system comprises:
   positioning the fastener system around the plurality of fibers such that a first portion of the plurality of fibers extends past a first edge of the fastener system and a second portion of the plurality of fibers extends past a second edge of the fastener system.

3. The method of claim 2, wherein cutting through the fastener system comprises:
   cutting through the fastener system, in a plane approximately normal to a longitudinal axis through the channel, to create the first fiber bundle and the second fiber bundle, wherein the first fiber bundle includes the first portion of the plurality of fibers and wherein the second fiber bundle includes the second portion of the plurality of fibers.

4. The method of claim 2, wherein cutting through the fastener system comprises:
   cutting through the fastener system, in a plane approximately normal to a longitudinal axis through the channel, to separate the fastener system into the first fastener that remains secured to the first portion of the plurality of fibers and the second fastener that remains secured to the second portion of the plurality of fibers.

5. The method of claim 1, wherein coupling the first fiber bundle with the second fiber bundle comprises:
   coupling the first fiber bundle and the second fiber bundle with an interfacing percentage of greater than about 50%.

6. The method of claim 1, wherein securing the plurality of fibers within the channel of the fastener system comprises:
   binding the plurality of fibers to the fastener system using a binding material, wherein the binding material comprises at least one of an adhesive, a potting agent, or a resin.

7. The method of claim 1, further comprising:
   polishing a first exposed end of the first fiber bundle and a second exposed end of the second fiber bundle prior to coupling the first fiber bundle with the second fiber bundle.

8. The method of claim 1, further comprising:
   aligning the first fiber bundle with the second fiber bundle prior to coupling the first fiber bundle with the second fiber bundle.

9. The method of claim 1, wherein cutting through the fastener system comprises:
   cutting through a surface feature on an outer surface of the fastener system to create the first fastener having a first set of alignment features and the second fastener having a second set of alignment features, wherein the first fastener is secured to the first fiber bundle and the second fastener is secured to the second fiber bundle.

10. The method of claim 9, further comprising:
    aligning the first set of alignment features of the first fastener with the second set of alignment features of the second fastener prior to coupling the first fiber bundle with the second fiber bundle.

11. The method of claim 1 wherein the packing configuration is a hexagonal packing configuration.

* * * * *